Figure 1:
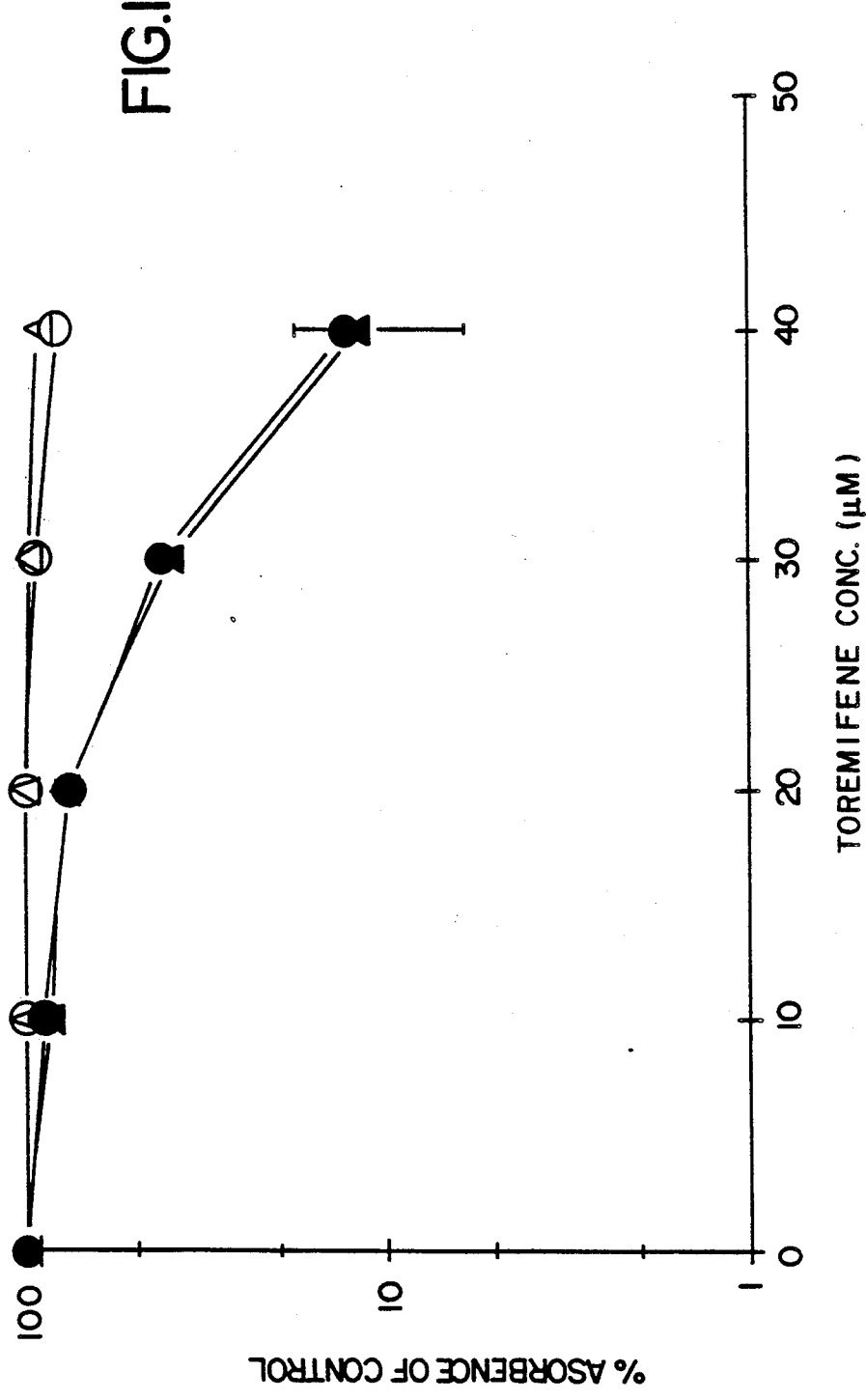

United States Patent [19]

Harris et al.

[11] Patent Number: 4,990,538
[45] Date of Patent: Feb. 5, 1991

[54] USE OF TOREMIFENE AND ITS METABOLITES FOR THE REVERSAL OF MULTIDRUG RESISTANCE OF CANCER CELLS AGAINST CYTOTOXIC DRUGS

[76] Inventors: Adrian L. Harris, 83 Kingston Road, Oxford OX2 64J, Great Britain; Lauri V. M. Kangas, Pasantie 3 B, 21280 Raisio, Finland; Michael W. DeGregorio, 93 Leatherman Trail, Hamden, Conn. 06518

[21] Appl. No.: 397,551

[22] Filed: Aug. 23, 1989

[51] Int. Cl.$^5$ .................................. A61K 31/135
[52] U.S. Cl. ................................ 514/648; 514/646
[58] Field of Search ...................... 514/646, 648, 650

[56] References Cited

PUBLICATIONS

Chemical Abstracts, vol. 111, p. 20, 1989, 89809b.

Primary Examiner—Mukund J. Shah
Assistant Examiner—D. D. Carr
Attorney, Agent, or Firm—Armstrong, Nikaido, Marmelstein, Kubovcik & Murray

[57] ABSTRACT

This invention relates to the use of a compound comprising toremifene or its metabolites N-demethyltoremifene or 4-hydroxytoremifene or its non-toxic pharmaceutically acceptable salts for the reversal of multidrug resistance of cancer cells to cytotoxic drugs in the treatment of cancer with such cytotoxic drugs.

3 Claims, 8 Drawing Sheets

EFFECT OF INCREASING CONCENTRATIONS OF TOREMIFENE IN CHO-KI(●—●,o—o) AND CHO-Adr(▲—▲, △—△) CELL LINES AFTER 24 HRS. EXPOSURE. CLOSED SYMBOLS, ABSENCE OF AAG (2mg/ml) OPEN SYMBOLS, PRESENCE OF AAG

USE OF TOREMIFENE AND ITS METABOLITES FOR THE REVERSAL OF MULTIDRUG RESISTANCE OF CANCER CELLS AGAINST CYTOTOXIC DRUGS

This invention relates to the use of toremifene and its metabolites N-demethyltoremifene (4-chloro-1,2-diphenyl-1-(4-(2-(N-methylamino)ethoxy)phenyl)-1-butene) and 4-hydroxytoremifene (4-chloro-1-(4-hydroxyphenyl)-2-phenyl-1-(4-(2-(N,N-dimethylamino)ethoxy)phenyl)-1-butene) for the reversal of multidrug resistance of cancer cells to cytotoxic drugs.

The treatment of human cancers with cytotoxic drugs is an important part of the modern clinical cancer treatment. The cytotoxic chemotherapy, although often initially effective, however, often ultimately fails because of development of resistant tumor cell clones. The resistance is developed typically simultaneously against several cytotoxic drugs and is therefore called multidrug resistance (MDR) (Deuchards KL, Ling V: P-glycoprotein and multidrug resistance in cancer chemothrapy. Seminars in Oncology, 1989, 16, 156–165; Pastan I, Gottesman M: Multiple-drug resistance in human cancer. NM. Engl. J. Med. 1987, 316, 1388–1393). The mechanism of MDR is not well known, but at least two cellular events have been suggested to coincide with MDR; 1) increased expression of a specific cell membrane glycoprotein with the molecular weight of 170 kD (gp170) and its mRNA (mdr-1) (Fuqua SAW, Moretti-Rojas IM, Schneider SL, Mcguire WL: P-glycoprotein expression in human breast cancer cells. Cancer res. 1987, 47, 2103–2106) and 2) decreased accumulation of cytotoxic drugs into the cells (Deuchards KL, Ling V: P-glycoprotein and multidrug resistance in cancer chemotherapy. Seminars in Oncology, 1989, 16, 156–165; Bell DR, Gerlich JH, Kartner N, Buick RN, Ling V: Detection of P-glycoprotein in ovarian cancer; a molecular marker associated with multidrug resistance. J. Clin. Oncol. 1985, 3, 311–315). These two events may well be associated and probably gp170 is the protein responsible for the increased efflux of cytotoxic drugs from the cell.

The reversal MDR would give very beneficial way to improve the results of cytotoxic treatments in human cancer. The reversal has been shown to be possible with compounds affecting the calmodulin, the main calcium binding protein in the cell membranes and inside the cells (Miller RL, Bukowski RW, Budd GT, et al, Clinical modulation of doxorubicin resistance by the calmodulin inhibitor, trifluperazine: A phase I/II trial. J. Clin. Oncol. 1988, 6, 880–888). Similarly altered activities of glutathione-S-transferase and lowered membrane potentials have been shown to be connected with MDR (Cowan KH: The role of glutathione-S-transferase in drug resistance. Proc. Amer. Assoc. Cancer Res. 1989, 30, 674; Kramer RA, Zakher J, Kim G: Role of the glutathione redox cycle in acquired and de novo multidrug resistance Science 1988, 241, 694–697).

Protein kinase C may also be of importance in the development of MDR. It has a crucial role in the transduction of variety of regulating signals into the cell and cytotoxic drugs have been reported to inhibit this protein (Palayoor ST, Stein JM Hait WN: Inhibition of protein kinase C by antineoplastic agents: implication for drug resistance. Biochem. Biophys. Res. Commun. 1987, 148, 718–725. Compounds, which affect the mechanisms known to reverse the MDR, are not commonly used clinically because of their toxicity at the dose ranges necessary to achieve the reversal of MDR. (Gottesman MM: Clinical trials of agents that reverse multidrug-resistance. J. Clin. Oncol. 1989, 7, 409–410).

The drug tamoxifen has recently been shown to possess activity for reversing MDR (Foster BJ, Grotzinger KR, McKoy WM, Rubinstein LV, Hamilton TC: Modulation of induced resistance to adriamycin in two human breast cancer cell lines with tamoxifen or perhexiline maleate. Cancer Chemother Pharmacol 22: 147–152, 1988.). Similar to the other chemosenziting agents, in vivo concentrations of tamoxifen necessary for reversing drug resistance may not be achieved without significant toxicity.

Toremifene (Fc-1157a) is an antiestrogenic compound with triphenylethylene structure. Its pharmacological properties, antiestrogenic and oncolytic effects, have been described e.g. in U.S. Pat. No. 4696949 and in the publications: Kallio et al: A new triphenylethylene compound, Fc-1157a. I Hormonal effects. Cancer Chemother. Pharmacol. 1986, 17, 103–108; Kangas et al: A new triphenylethylene compound, Fc-1157a. II Antitumor effects. Cancer Chemother. Pharmacol. 1986, 17, 109–113; Ebbs SR, Roberts JV, Baum M: Alternative mechanism of action of "anti-oestrogens" in breast cancer. Lancet 1987, ii, 621).

The present invention relates to a new use of toremifene and its metabolites N-dsmethyltoremifene and 4-hydroxytoremifene. These compounds, particularly toremifone can successfully be used to reverse the resistance to cytotoxic drugs because clinically effective doses can be achieved due to the relatively low toxicity of these compounds even at high doses. Both acquired and natural resistance are affected by the compounds. This property is important and can greatly improve the clinical efficacy of cytotoxic therapy. The main features of the present invention are as follows:

1. The compound, particularly toremifene changes multidrug resistant cancer cells sensitive to cytotoxic drugs, especially to doxorubicin, but also to etoposide, cisplatinum and cyclophosphamide.

2. The combination of toremifene and cytotoxic drugs does not influence in marked extent on the toxicity of either treatment alone.

3. Although toremifene, when used as a single treatment, has antitumor activity especially in breast cancer, the reversal of MDR is not limited to breast cancer. In fact, all types of tumors can be equally well be treated with the combination.

4. In reversing the MDR, toremifene is an addition to the cytotoxic chemotherapy, which otherwise in indicated. Therefore toremifene does not change the principles of the established cancer chemotherapies.

5. In reversing the MDR high concentrations of toremifene are more effective than low concentrations. Therefore the dose of toremifene for reversal of MDR should be high. It has been shown in clinical phase I, II and III studies that toremifene is very safe drug also at such dose levels which are required to achieve the reversal of MDR. This is a unique property which has not been described to any other MDR reversing agent.

The clinical treatment schedule can be described as follows: Toremifene should be used at a high dose, preferably the maximum tolerated dose. The dose range is expected to be about 60 to 600 mg/day/adult person. The preferable dose is estimated to about 400 mg/day/adult person. The drug is preferably administered perorally as tablets.

Schedule of MRD reversal with toremifene:

1. Toremifene is started 5 to 10 days before the cytotoxic treatment to achieve as high blood and tissue concentrations as possible.
2. Cytotoxic treatment is given normally.
3. Toremifene administration is continued up to the end of the cytotoxic treatment period.

Because cytotoxic drugs are commonly given in cycles (a treatment period of about 1 day to 2 weeks followed by an interval of about 2 weeks to 3 months), toremifene treatment is also given in cycles so that the interval for the drugs starts simultaneously. Because toremifene administration starts 5 to 10 days before the cytotoxic treatment, the treatment period for toremifene will be 5 to 10 days longer than for the cytotoxic treatment.

The above suggested treatment schedule will apply for N-demethyltoremifene and 4-hydroxytoremifene as well. N-demethyltoremifene and 4-hydroxytoremifene are metabolites of toremifene and effective concentrations for MDR reversal are reached during the treatment period with toremifene.

EXPERIMENTS

I. In Vito Tests

Initial cell growth studies were carried out to investigate the effect of combination toremifene +doxorubicin in doxorubicin sensitive and resistant cells. Cell cultures were carried out using wild type CHO-K1 cells as well as CHO-Adr cells, the latter being selected by a series of step-wise selections of doxorubicin resistant clones in presence of 0.4 ug/ml of doxorubicin. The cell line was resistant to doxorubicin, but simultaneously cross-resistant to vinca alkaloids, daunorubicin, actinomycin D and colchicine. The resistant cells were stable in cell culture in the absence of doxorubicin. Both cell lines were cultivated in Hams F10 medium supplemented with 5% newborn calf serum, 5% foetal calf serum, antibiotics and 3mM glutamine. The cells were maintained as monolayer cultures 37° C. under 5% $CO_2$. Drug sensitivity in CHO-K1and CHO-Adr cells was assessed by a semi-automated colorimetric MTT assay. The assay is dependent on the cellular reduction of MTT (3-U4,5-dimethylthiazol-2-ylA-2,5-diphenyl tertazolium bromide, thiazolyl blue) by the mitochondrial dehydrogenase of viable cells to a blue formazan product which was measured spectrophotometrically. The cells were seeded on 96-well plates and allowed to settle for 12 hours at 37° C. in 5% $CO_2$. Appropriate drug concentrations diluted in growth medium were added for 24 hours. Toremifene was dissolved in 95% ethanol stock solution, doxorubicin stock solution was prepared in water. Ethanol concentration in the final culture medium never exceeded 0.1% and did not affect cell growth. The cells were incubated with the drugs for 24 hours, after which the cells were washed twice with phosphate buffered saline before being placed in 200 μl fresh medium for a further 48 hours. At the end of this incubation 0.1 mg MTT was added to each well and incubated for 4 hours. The medium was carefully aspirated and the crystals were solubilised in 100 μl DMSO (dimethyl sulfoxide). Absorbances at 540 nm were read immediately on an ELISA Multiskan reader. The results were expressed as a percentage of absorbance of drug treated cells compared to controls.

As toremifene is bound in some extent to $α_1$-acid glycoprotein (AAG), this protein was added to the growth medium in some test series to evaluate if it can influence the reversal of MDR.

RESULTS

The results of these assays have been presented in Table 1 and in FIGS. 1–6.

Toxicity of toremifene:

The CHO-K1 cell lines and the CHO-Adr lines were equally sensitive to 24 hours exposure of toremifene. Toxicity was detectable above 10 μM toremifene. AAG added at concentrations equivalent to that found in patients with cancer (2 mg/ml) protected both cell lines from toremifene toxicity (FIG. 1).

Figure 2:
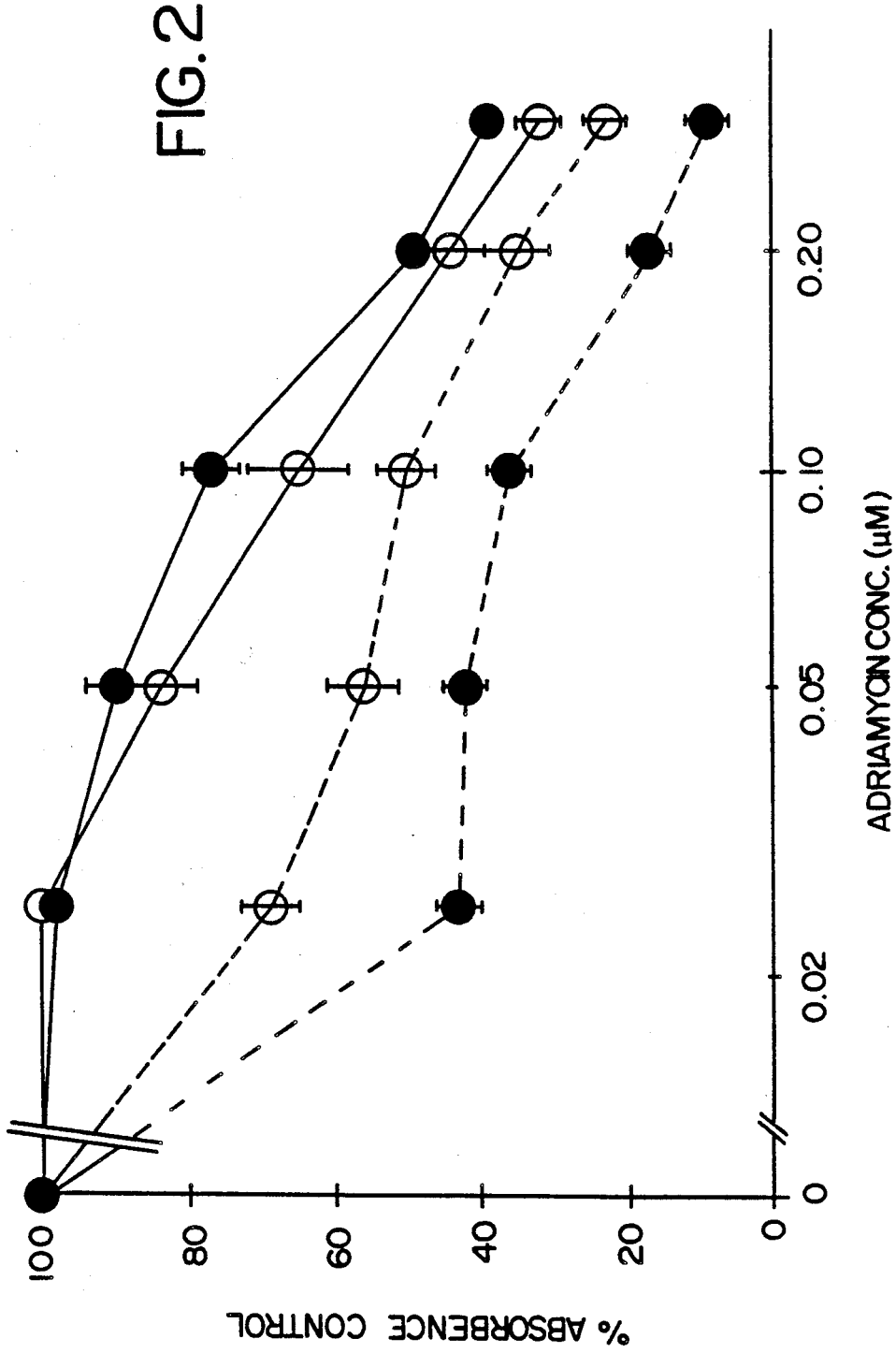

Potentiation of doxorubicin (Adriamycin) cytotoxicity by toremifene:

There was incremental potentiation of doxorubicin toxicity in CHO-K1 cells with increasing doses of toremifene from 1 to 10 μM. This effect was most marked at the lower doxorubicin concentrations (FIG. 2).

Figure 3:
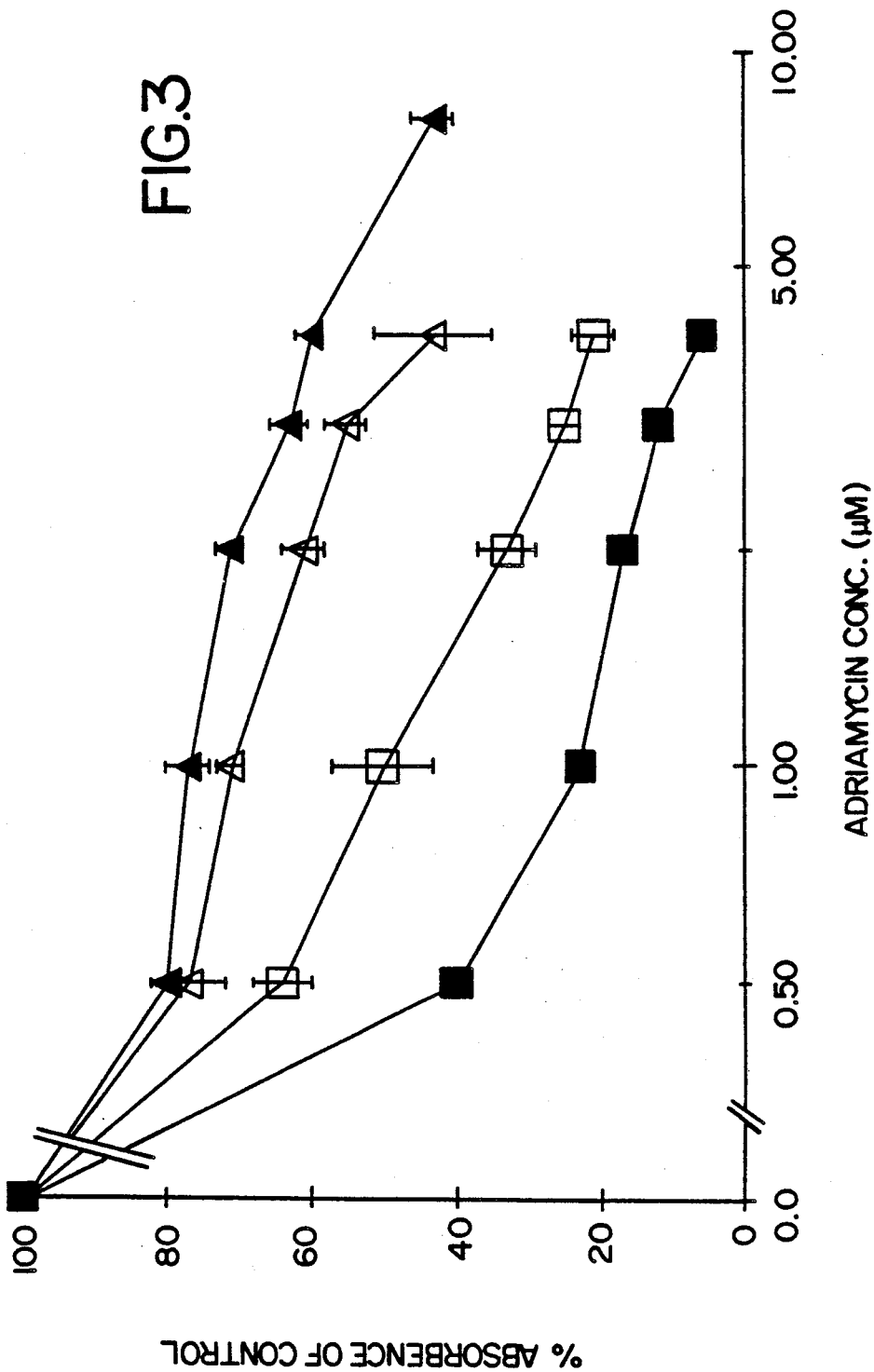

Similarly there was potentiation of the CHO-Adr cells by toremifene although the degree of potentiation was greater (FIG. 3).

Figure 4:
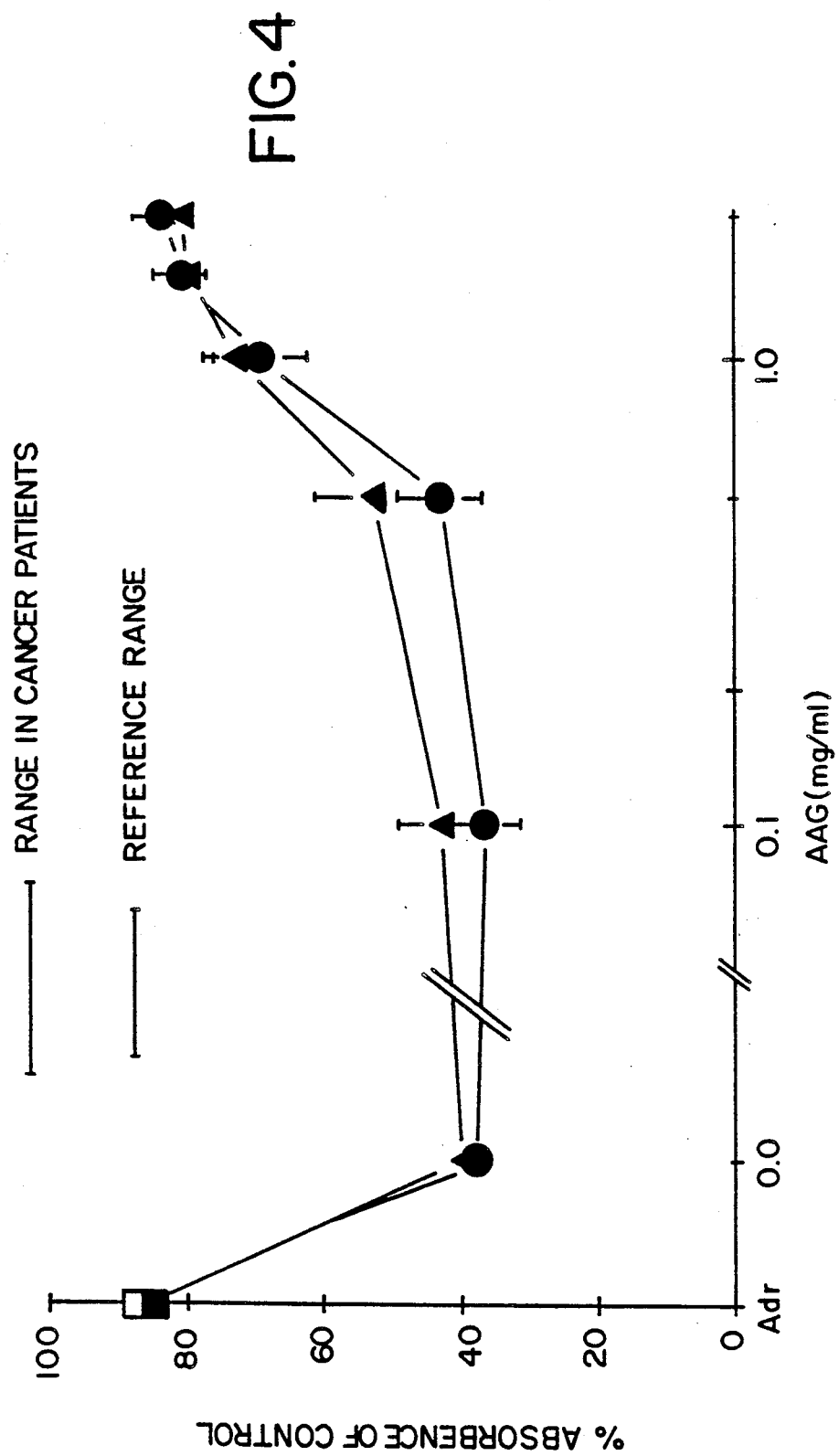
Figure 5:
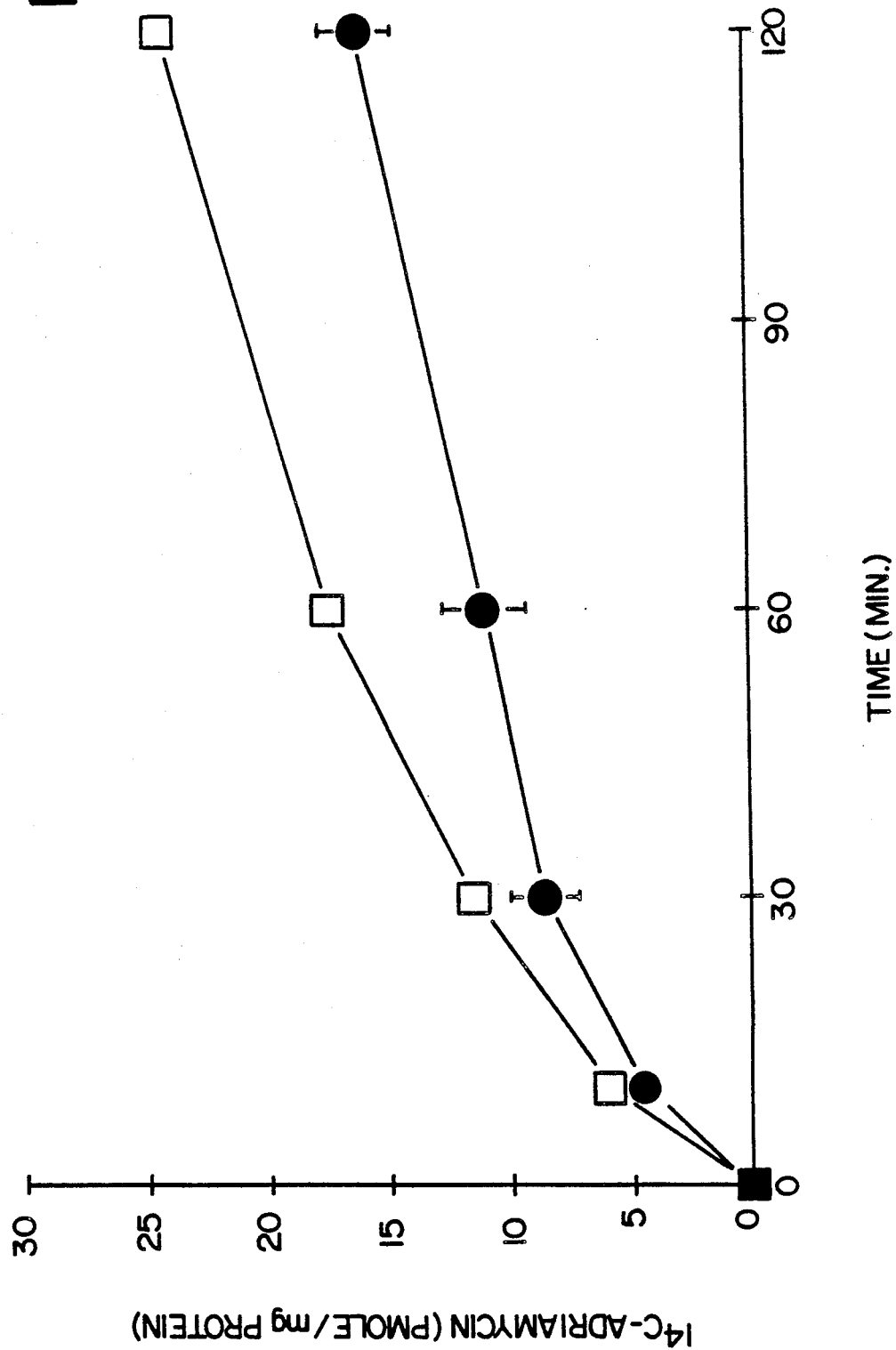

Effect of AAG on potentiation of doxorubicin toxicity by toremifene:

CHO-K1 and CHO-Adr cell lines were incubated with concentrations of doxorubicin which were equitoxic in the absence of toremifene and which produced similar reduction in survival in the presence of 10 μM toremifene (FIG. 4). The effect of AAG in the concentration of 0.1 to 2 mg/ml was assessed on the potentiation produced by toremifene. At concentrations of AAG above 0.5 mg/ml the potentiation effect of toremifene was gradually reversed and at the highest level 2 mg/ml there was no longer any effect of toremifene on doxorubicin toxicity. This occurred with both the resistant and wild-type cell lines.

Figure 6:
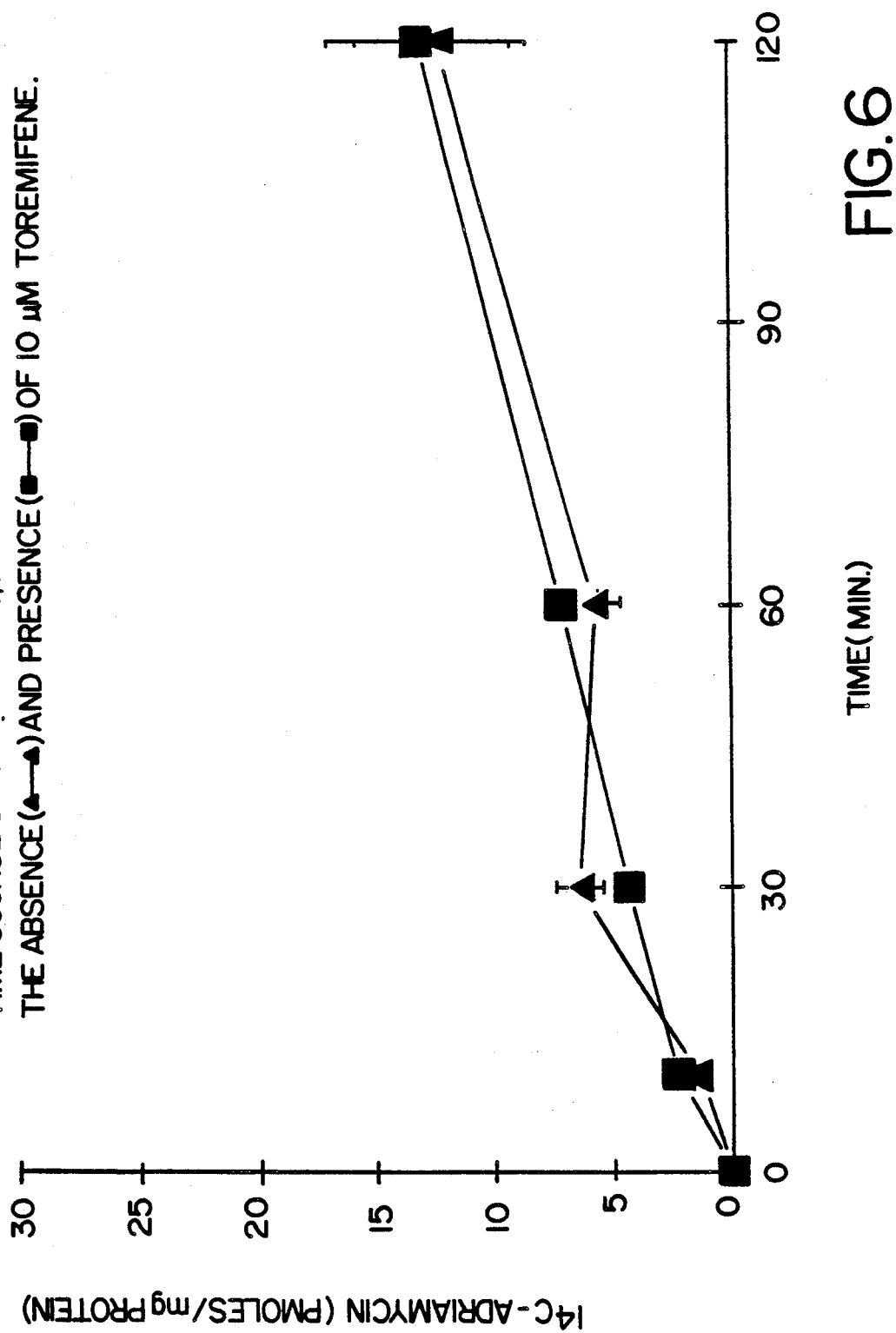

The effects of toremifene on doxorubicin transport:

2 μM toremifene enhanced drug accumulation of 1 μM doxorubicin in wild-type CHO-K1 cells (FIG. 5) but not in resistant cells (FIG. 6).

Relative potentiation of doxorubicin toxicity by toremifene in CHO-K1 and CHO-Adr cells:

There was a steep dose response curve for potentiation with increasing concentrations of toremifene and this was greater for the resistant than the wild-type cells (Table 1).

TABLE 1

Effect of Toremifene on the sensitivity of CHO-K1 and CHO-Adr cells to Adriamycin

| Drug | Adriamycin $IC_{50}$ (μM) | | | |
|---|---|---|---|---|
| | CHO-K | fold decrease in[b] cytotoxic concentration | CHO-Adr | fold decrease in cytotoxic concentration |
| Adriamycin + 1 μM Toremifene | 0.16 | 1.5 | 3.5 | 2.0 |
| Adriamycin + 5 μM Toremifene | 0.1 | 2.4 | 1.0 | 6.4 |

TABLE 1-continued

Effect of Toremifene on the sensitivity of CHO-K1 and CHO-Adr cells to Adriamycin

| | Adriamycin IC$_{50}$ ($\mu$M) | | | |
|---|---|---|---|---|
| Drug | CHO-K | fold decrease in[b] cytotoxic concentration | CHO-Adr | fold decrease in cytotoxic concentration |
| Adriamycin + 10 $\mu$M Toremifene | 0.02 | 12 | 0.4 | 16 |

[a]Cells were exposed to drug(s) for 24 hours as described in the text and cell viability measured by the MTT assay. Each value is a mean of at least 3 experiments.
[b]Calculated by dividing the IC$_{50}$ of controls by that of toremifene treated cells.

Combination of toremifene and doxorubicin in 2 human ovarian cancer cell lines developed in Farmos' cancer research laboratory and in one human melanoma developed by Dr. Grenman in Turku University, Dept. of Gynecology.

METHOD

Two human ovarian cell lines were established in vitro from fresh serous ovarian cancer tissues. The lines are coded HOV-007 and HOV-018. The cells were cultivated in Eagle's MEM containing 1% unstripped foetal calf serum. The assays were carried out at 37° C. in 5% $CO_2$ on 96 well plates. Doxorubicin was dissolved in growth medium and toremifene in 95% ethanol, from which it was diluted with growth medium. The concentration of ethanol never exceeded 0.07% and it did not influence the growth of the cells. The number of living cells was quantitated by bioluminescence method, which has been described earlier (Kangas L, Nieminen A-L, Grönroos M: Bioluminescence of cellular ATP: a new method for evaluation of cytotoxic agents in vitro. Med. Biol. 1984, 62, 338–343).

RESULTS

Results have been presented in the three next tables.

TABLE 2

Toremifene and doxorubicin in cell line HOV-007. Number of living cells (percent of control values) has been presented. Number of cells was quantitated after 3 days' cultivation.

| | Doxorubicin ($\mu$g/ml) | | | |
|---|---|---|---|---|
| Toremifene ($\mu$M) | 0 | 0.1 | 0.3 | 1.0 |
| 0 | 100 | 87 | 64 | 41 |
| 1.0 | 95 | 71 | 44 | 19 |
| 3.0 | 71 | 46 | 31 | 3 |
| 10.0 | 66 | 47 | 29 | 4 |

TABLE 3

Toremifene and doxorubicin in cell line HOV-018. Doxorubicin concentrations 0.1 and 0.3 $\mu$g/ml were tested. For explanations: see previous table.

| | Doxorubicin ($\mu$g/ml) | | |
|---|---|---|---|
| Toremifene ($\mu$M) | 0 | 0.1 | 0.3 |
| 0 | 100 | 96 | 89 |
| 1.0 | 104 | 93 | 62 |
| 3.0 | 99 | 78 | 49 |
| 10.0 | 97 | 77 | 47 |

The cells were almost resistant to both compounds separately, but were markedly sensitized by using the combination.

TABLE 4

Human melanoma UV-me-1
The cells were cultivated for 2 days. The concentrations of toremifene and doxorubicin have been indicated in next table.

| | Doxorubicin ($\mu$g/ml) | | |
|---|---|---|---|
| Toremifene ($\mu$M) | 0 | 0.1 | 1.0 |
| 0 | 100 | 74 | 9 |
| 0.5 | 97 | 74 | 7 |
| 5.0 | 32 | 26 | 0 |

Although this cell line is relatively sensitive to doxorubicin alone, the combination, especially in low doxorubicin and high toremifene concentrations is clear.

The efficacy of the combination of toremifene and doxorubicin may vary in different cell lines. However, the best efficacy is achieved with high concentrations. If this is valid also clinically, high doses of toremifene and cytostatics should be used to reach the most effective antitumor effect.

MCF-7 is an established human breast cancer cell line. It is estrogen receptor positive and is widely used in vitro model in breast cancer investigations. The original cell line was obtained from Dr. Ken Cowen (National Cancer Institute, Bethesda, Maryland, USA). Doxorubicin resistant mutant MCF-7/DOX cell line was developed by stepwise exposure of cells to increasing concentrations of doxorubicin. Cells were growth in Corning 75-cm$^2$ tissue flasks and were maintained in exponential growth using RPMI 1640 medium supplemented with 5% fetal bovine serum in 5% $CO_2$ and 95% air. Inhibition of cellular proliferation was determined using methods previously described (Ford JM, Prozialeck WC, Hait WN: Structural features determining activity of phenothiazines and related drugs for inhibition of cell growth and reversal of multidrug resistance. Mol. Pharmacol. 1989, 35, 105–115). The cells were cultivated in 100 ul volumes in 96-well microtiter plates. The principle of the method was to cultivate cells in the presence of the drugs/ drug combinations for 48 hours. After this time the living cells were stained with methylene blue and quantitated spectrophotometrically using microtiter plate reader (Titertek Model MCC/340) interfaced to an Apple IIe computer. Inhibition of the cell growth is expressed as a percentage of absorbance of vehicle treated control cultures. Human plasma samples were obtained from patients participating clinical phase I studies receiving 10, 20, 40, 60, 200 or 400 mg toremifene daily for eight weeks. Ultrafiltrate from the plasma was prepared by placing plasma specimens in Amicon CF-10 filters (MW cutoff 10 000) followed by centrifugation at 5000×g for 20 minutes. The ultrafiltrates were used in order to study if the concentrations achieved clinically were able to sensitize MCF-7/DOX. Part of the growth medium was replaced by plasma ultrafiltrate and the cells were allowed to grow for 4 days, at which time they were stained and quantitated as described above.

In addition to toremifene, the metabolites of toremifene, N-demethyltoremifene and 4-hydroxytoremifene as well as tamoxifen were used. Like this it was possible to study the relation of antiestrogenicity and MDR reversing ability.

Figure 7:
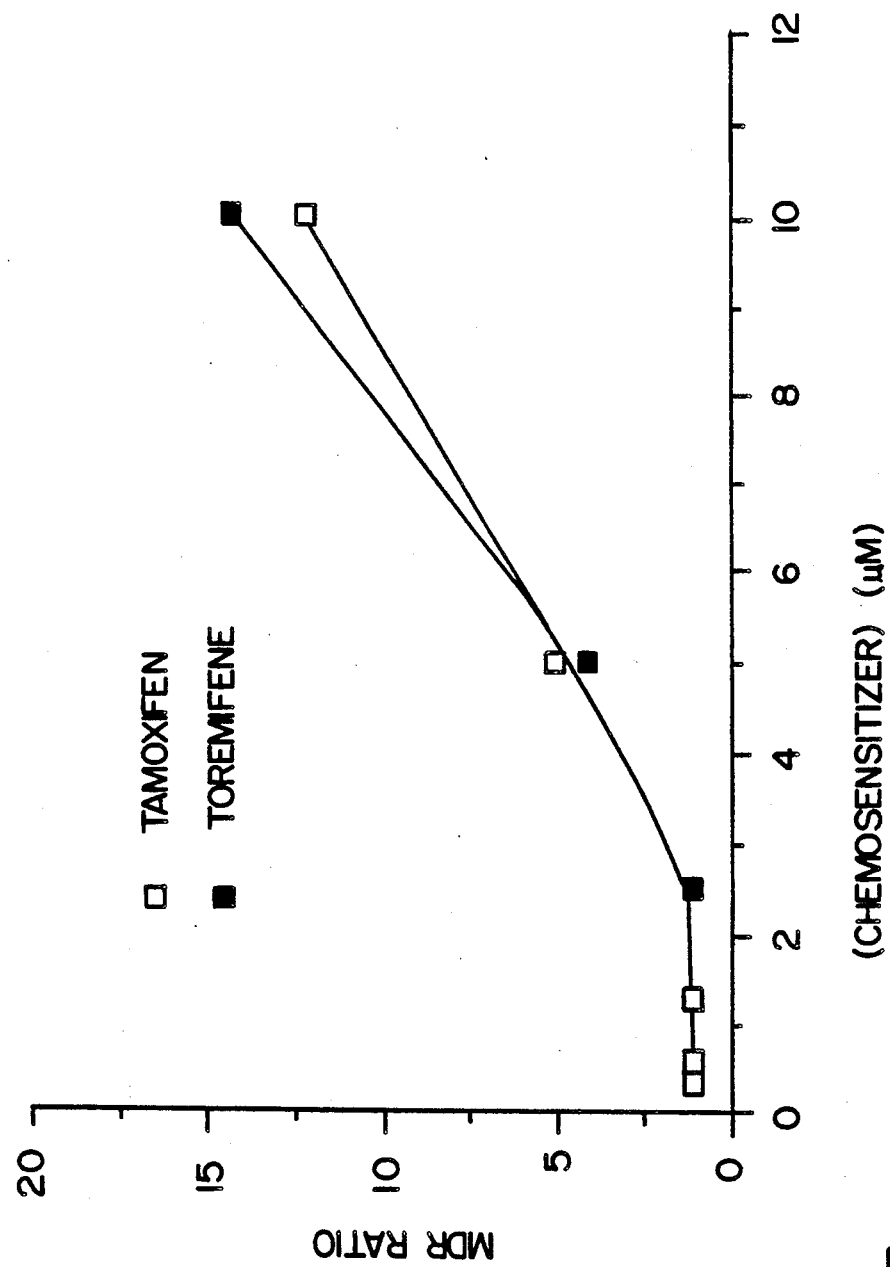
Figure 8A:
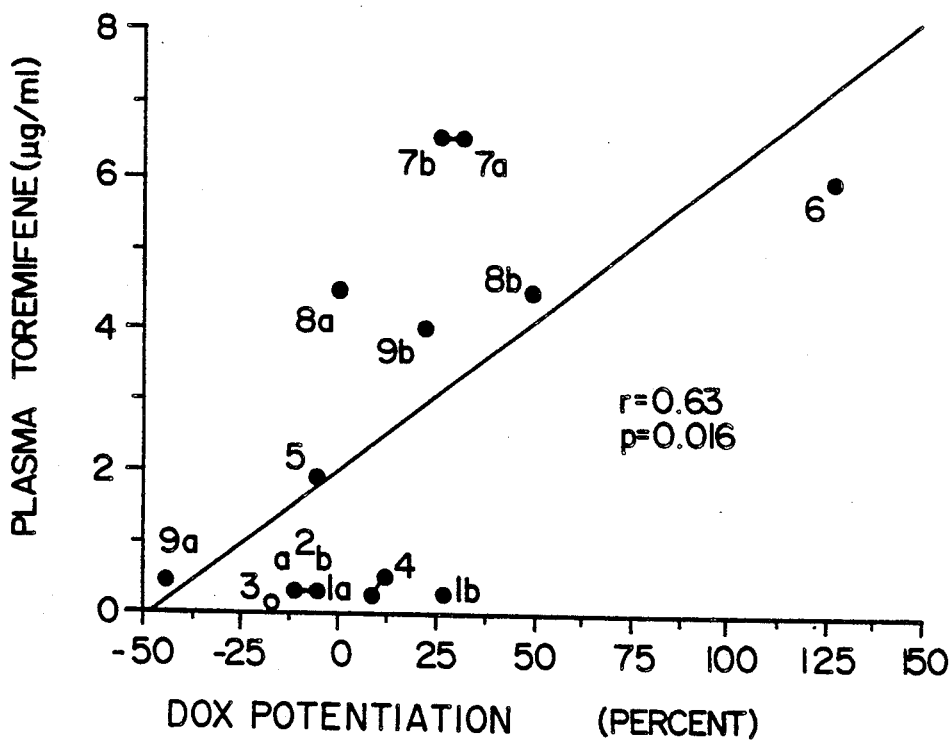
Figure 8B:
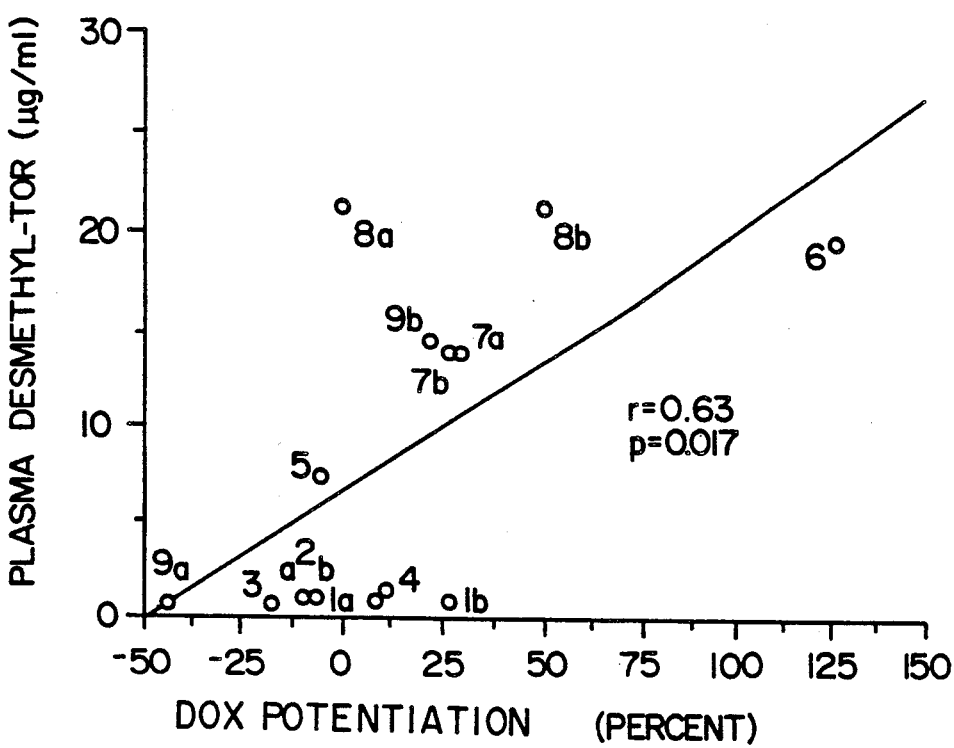

Tamoxifen, toremifene and N-demethyltoremifene were almost equally effective in reversing MDR in MCF-7/DOX cells as shown in Table 5 and FIG. 7. 4-hydroxytoremifene, which has lower intrinsic estrogenicity and is more potent antiestrogen was slightly less effective. This indicates that MDR reversal is not due to the antiestrogenic property of the compounds. The concentrations of toremifene +N-demethyltoremifene (more than 20 $\mu$M) in clinical samples were well above the concentration (10 $\mu$M) needed for reversal of MDR. A clear concentration-dependency in MDR reversing effect in patients' sera was found (FIG. 8.). This indicates that the higher dose of toremifene is the better in the MDR reversing effect. In clinical practice it is therefore indicated to give toremifene in as high doses as possible. The maximal tolerated dose is according to the clinical phase I trials about 400 to 600 mg daily. These doses give rise to sufficient serum and tissue concentrations for effective MDR reversal. Importantly, such high concentrations cannot be reached in tamoxifen treatment due to the higher toxicity of tamoxifen.

TABLE 5

Potentiation of doxorubicin activity in MDR cells by toremifene and its metabolites.

| Drug | ($\mu$g/ml) | Drug Alone | Pre-dicted | Actual | Potential |
|---|---|---|---|---|---|
| toremifene | 3.0 | 15 | 24 | 38 | 58 |
|  | 1.5 | 12 | 21 | 31 | 48 |
| N-desmethyltore-mifene | 1.5 | 20 | 28 | 40 | 43 |
|  | 0.6 | 12 | 21 | 28 | 33 |
| 4-hydroxytore-mifene | 1.5 | 34 | 41 | 45 | 10 |
|  | 0.6 | 18 | 26 | 28 | 8 |

Inhibition of cell growth (% control) +1 $\mu$M doxorubicin

II. In Vivo Tests

Subrenal capsule assay

Pieces of fresh human tumors were implanted under the outer capsule of mouse kidney. Mice were treated with different combinations of cytotoxic drugs (doses preselected according to toxicity of each combination), with or without toremifene (150 mg/kg p.o.). Control animals received saline injections. The drugs were given on five consecutive days after the inoculation of the tumors. The sizes of the tumor pieces were measured by stereo microscope equipped with ocular micrometer immediately after inoculation (initial size) and on the sixth day when the animals were killed (final size). The difference final size - initial size describes the growth or regression of the tumor. The measuring unit was ocular micrometer unit (omu). 10 omu is identical to 1.0 mm. In addition to the tumor size, the weight gain of the animals was measured. The weight gain describes the toxicity of the treatment. In general, the ratio final weight/ pretest weight should be more than 0.80. Otherwise the toxicity is considered unacceptable.

TABLE 6

Effect of toremifene in combination with cytotoxic drugs in subrenal capsule assay (SRCA) in fresh human tumor samples.

| | Change in the tumor size (omu) during the 5 days' treatment (mean ± sd) | | |
|---|---|---|---|
| Tumor type | Control | Cytotoxic Combination | Cytotoxic Comb. + tore |
| Ovarian ca. | 5.2 ± 1.6 | −0.3 ± 0.7 (CAP) | −0.4 ± 1.0 |
| Ovarian ca. | 4.6 ± 1.8 | 0.6 ± 1.6 (CAP) | −0.8 ± 1.6 |
| Ca. peritonei | 2.0 ± 1.4 | 2.1 ± 1.7 (CAP) | −0.2 ± 0.1 |
| Melanoma | 4.3 ± 1.9 | −0.8 ± 1.2 (PE) | −1.5 ± 1.4 |

CAP = Cyclophosphamide + doxorubicin + cisplatinum
PE = Cisplatinum + etoposide
Weight gain of the animals during the assay in the same animals was as follows (respectively):

| Ovarian ca. | 0.87 ± 0.02 | 0.86 ± 0.05 | 0.84 ± 0.01 |
| Ovarian ca. | 1.02 ± 0.03 | 0.92 ± 0.00 | 0.91 ± 0.05 |
| Ca. peritonei | 0.93 ± 0.03 | 0.92 ± 0.01 | 0.90 ± 0.03 |
| Melanoma | 0.97 ± 0.02 | 0.87 ± 0.01 | 0.90 ± 0.02 |
| Mean | 0.95 ± 0.06 | 0.89 ± 0.03 | 0.89 ± 0.03 |

The results indicated that toremifene can increase the sensitivity to cytotoxic drugs in human tumors especially in cases when the tumor is partly or completely resistant to the cytotoxic drug combinations. The weight gain of the animals during the array was not influenced by toremifene addition.

Schedule dependency of antitumor effect of toremifene and doxorubicin was studied in solid mouse tumors. Lewis Lung (LL) or melanoma B-16 tumor cells, $2 \times 10^6$ cells/animal, were inoculated intramuscularly to female C-57 mice. Tumors were allowed to grow to the mean diameter of 1.5 cm after which toremifene/doxorubicin treatments were started as indicated in the next tables. Tumor size was measured before treatment and after 10 days in 2 dimensions and the mean was considered as tumor diameter. Weight of the animals was also recorded.

TABLE 7

| Treatment schedule | Change of tumor diameter (mm) | Change of body weight (g) |
|---|---|---|
| Control group, saline p.o. days 1-5 | +5.6 | +10 |
| Toremifene 150 mg/kg p.o. days 1-5 | +5.4 | +6 |
| Doxorubicin 3 mg/kg s.c. days 1-5 | +2.0 | −2 |
| Doxorubicin 3 mg/kg s.c. days 6-10 | +3.7 | +10 |
| Toremifene 150 mg/kg p.o. days 1-5 + Doxorubicin 3 mg/kg s.c. days 1-5 | −0.6 | −5 |
| Toremifene 150 mg/kg p.o. days 1-5 + Doxorubicin 3 mg/kg s.c. days 6-10 | +1.4 | −4 |

The results indicate that toremifene and doxorubicin have best antitumor effect when given simultaneously in this tumor model. Similar results were obtained in B-16 melanoma in G57mice:

TABLE 8

| Treatment schedule | Change of tumor size (mm) | Change of body weight (g) |
|---|---|---|
| Control group, saline p.o. days 1-5 | +5.0 | +10 |
| Toremifene 150 mg/kg p.o. days 1-5 | +3.2 | +9 |
| Doxorubicin | +1.9 | −5 |

TABLE 8-continued

| Treatment schedule | Change of tumor size (mm) | Change of body weight (g) |
|---|---|---|
| 3 mg/kg s.c. days 1-5 Doxorubicin | +3.1 | −2 |
| 3 mg/kg s.c. days 6-10 Toremifene 150 mg/kg p.o. days 1-5 + Doxorubicin 3 mg/kg s.c. days 1-5 | −0.7 | −5 |
| Toremifene 150 mg/kg p.o. days 1-5 + Doxorubicin 3 mg/kg s.c. days 6-10 | +1.0 | −5 |

We have demonstrated in this study that the sensitivity to doxorubicin in wild-type CHO cells (CHO-K1) and its MDR mutant (CHO-Adr) can be increased by toremifene concentrations which do not inhibit cell growth on their own. The degree of potentiation was far greater in the CHO-Adr cell line than in the parent cell line. The exact mechanism of modulation of doxorubicin cytotoxicity by toremifene is, however, unclear. Since there were no measurable levels of oestrogen receptors in the two cell lines (results not shown), we conclude that the reversal of MDR is independent of the oestrogen receptor status of the two cell lines. Sutherland et al (Nature 288:273-275) have observed that growth inhibitory effects mediated by high doses of tamoxifen in cultured cells could not be reversed by oestradiol, and suggest they involve mechanisms independent of the oestrogen receptor system. Ramu et al (Cancer Res. 44:4392-4395) have demonstrated reversal of MDR by triparonol analogues such as tamoxifen, clomiphene, nafoxidine and others. They suggest that the increased membrane rigidity reported in MDR cell membranes is decreased by the triparonol analogues, which accounts for easier diffusion of doxorubicin and enhances its cytotoxicity. Foster et al (Chemother. Pharmacol. 22:147-152) have reported modulation of multidrug resistance in an MCF-7 oestrogen receptor positive breast cancer cell line with 10 μM tamoxifen or perhexilene maleate. Since the addition of 50 nM estradiol did not attenuate the effects of tamoxifen, they have suggested that reversal of MDR by tamoxifen is not oestrogen-dependent. However, there was no increase in C14-doxorubicin accumulation, raising the possibility that tamoxifen (and other analogues) may modulate MDR by mechanisms other than increasing intracellular accumulation of the anticancer drugs to which the cell is resistant.

Protein kinase C (PKC) is a high affinity phorbol ester receptor. Phorbol esters and other tumour promoters function by acting as diglyceride substituents and active PKC in vitro and in vivo. PKC is believed to transduce a variety of growth promoting signals and may have an important role in tumour promotion. The importance of PKC in regulation of cell growth suggests that PKC inhibitors could prove to be effective anti-proliferative agents. O'Brian et al (J. Nat. Cancer Inst. 80: 1628-1633.) have reported (a) inhibition of rat PKC activity in vitro by tamoxifen and its principal metabolites 4-hydroxy tamoxifen which is mediated by the compounds binding to the catalytic domain of the enzyme and (b) the inhibitory potencies against PKC activity correlates with the oestrogen irreversible cytotoxic effects shown in the MCF-7 cell line. Horgan et al (Biochem. Pharm. 35: 4463-4465.) have shown inhibition of PKC activity in vivo by tamoxifen. These results, therefore, strongly suggest that inhibition of PKC may play an important role in the antitumour effect and modulation of MDR by toremifene. At highest AAG concentration, cell viability was no different from that when doxorubicin alone was present. Therefore AAG at high concentrations can prevent the modulatory effect of toremifene on doxorubicin cytotoxicity.

The clinical implications of this study are that toremifene and its metabolites could prove an effective cytotoxic agent as well as a modulator of multidrug resistance, the limiting factor to its effectiveness could be high levels of AAG. Clinical trials with the addition of toremifene or its metabolite in a chemotherapy regimen could increase the therapeutic index of the anticancer agents, regardless of the oestrogen receptor status.

This study represents the first report of clinically relevant concentrations of chemosensitizers being achieved and maintained in humans. These results strongly suggest that toremifene and its metabolites may be uniquely suited for use as a clinical modulator of tumor drug resistance in combination with other cytotoxic agents in humans.

We claim:

1. A method for reversing the multidrug resistance of cancer cells to a cytotoxic drug in the treatment of cancer with the cytotoxic drug, which comprises administering a multidrug resistance reversal effective amount of toremifene, N-demethyltoremifene or 4-hydroxytoremifene, or a non-toxic pharmaceutically acceptable salt thereof, to a patient having multidrug resistant cancer cells when treating the patient with the cytotoxic drug.

2. The method according to claim 1, wherein the compound is toremifene.

3. The method according to claim 1, wherein the cytotoxic drug is doxorubicin.

* * * * *